(12) United States Patent
Shim et al.

(10) Patent No.: US 9,945,898 B2
(45) Date of Patent: Apr. 17, 2018

(54) METHOD AND DEVICE FOR MEASURING INTERNAL QUANTUM EFFICIENCY OF AN OPTICAL ELEMENT

(71) Applicant: ETAMAX. CO., LTD, Gyeonggi-do (KR)

(72) Inventors: Jong-In Shim, Seoul (KR); Dong Pyo Han, Gyeonggi-do (KR); Hyun Don Jung, Gyeonggi-do (KR)

(73) Assignee: ETAMAX.CO., LTD (KR)

( * ) Notice: Subject to any disclaimer, the term of this patent is extended or adjusted under 35 U.S.C. 154(b) by 514 days.

(21) Appl. No.: 14/443,518

(22) PCT Filed: Jul. 31, 2013

(86) PCT No.: PCT/KR2013/006869
§ 371 (c)(1),
(2) Date: May 18, 2015

(87) PCT Pub. No.: WO2014/021623
PCT Pub. Date: Feb. 6, 2014

(65) Prior Publication Data
US 2015/0323463 A1 Nov. 12, 2015

(30) Foreign Application Priority Data

Jul. 31, 2012 (KR) .................. 10-2012-0084108
Jul. 30, 2013 (KR) .................. 10-2013-0090436

(51) Int. Cl.
*G06F 11/30* (2006.01)
*G01R 31/26* (2014.01)
(Continued)

(52) U.S. Cl.
CPC ..... *G01R 31/2635* (2013.01); *G01N 21/6489* (2013.01); *G01J 2001/4247* (2013.01); *G01N 2201/062* (2013.01)

(58) Field of Classification Search
CPC .................................................. G01R 31/2635
See application file for complete search history.

(56) References Cited

U.S. PATENT DOCUMENTS 8,600,705 B2 * 12/2013 Shim .................. G01N 21/6489
702/179

FOREIGN PATENT DOCUMENTS

JP   2007-088389       4/2007
JP   2007088389    *  4/2007
(Continued)

OTHER PUBLICATIONS

International Search Report for International Patent Application No. PCT/KR2013/006869, dated Sep. 30, 2013.

*Primary Examiner* — Phuong Huynh
(74) *Attorney, Agent, or Firm* — McAndrews, Held & Malloy, Ltd.

(57) ABSTRACT

A method for measuring the efficiency of an optical element is disclosed. The intensity of the light emitted from the optical element is measured by applying an injection current to the optical element, a relative radiative efficiency is calculated from a ratio of the intensity of the emitted light to the injection current, the maximum relative radiative efficiency and the maximum injection current corresponding to the maximum relative radiative efficiency are obtained, a reference injection current for minimizing an amount of change of a recombination coefficient in an active layer of the optical element in correspondence with a carrier density change in the active layer of the optical element is extracted from data of injection currents that are equal to or less than the maximum injection current and data of relative radiative efficiencies that are equal to or less than the maximum relative radiative efficiency, a reference internal quantum efficiency of the optical element is calculated from the reference injection current, and internal quantum efficiencies (Continued)

of the optical element in various injection currents are calculated from the reference internal quantum efficiency.

8 Claims, 12 Drawing Sheets

(51) Int. Cl.
*G01N 21/64* (2006.01)
*G21C 17/00* (2006.01)
*G01J 1/42* (2006.01)

(56) References Cited

FOREIGN PATENT DOCUMENTS

| JP | 2007-263624 | 10/2007 |
| KR | 10-2009-0053186 | 5/2009 |
| KR | 10-2011-0083871 | 7/2011 |
| KR | 10-2012-0081717 | 7/2012 |

* cited by examiner

METHOD AND DEVICE FOR MEASURING INTERNAL QUANTUM EFFICIENCY OF AN OPTICAL ELEMENT

CROSS-REFERENCE TO RELATED APPLICATIONS/INCORPORATION BY REFERENCE

This application is a 371 of International Patent Application No. PCT/KR2013/006869, filed on Jul. 31, 2013, entitled "METHOD AND DEVICE FOR MEASURING INTERNAL QUANTUM EFFICIENCY OF AN OPTICAL ELEMENT", which claims priority to Korean Application No. 10-2013-0090436, filed Jul. 30, 2013, entitled "METHOD AND DEVICE FOR MEASURING INTERNAL QUANTUM EFFICIENCY OF LED", and Korean Application No. 10-2012-0084108, filed Jul. 31, 2012 entitled "METHOD AND DEVICE FOR MEASURING INTERNAL QUANTUM EFFICIENCY OF AN OPTICAL ELEMENT". The above-identified applications are hereby incorporated herein by reference in their entirety.

TECHNICAL FIELD

The present invention disclosed herein relates to an optical element, and more particularly, to a method and a device for measuring internal quantum efficiency of a light emitting diode.

BACKGROUND ART

In general, a light emitting diode (LED) is widely used as a light source because it has characteristics of small size, low power consumption, and high reliability. A compound semiconductor such as InGaSaP, AlGaAs, GaAlP, GaP, InGaAlP or GaN is used for the LED. The LED includes an N-type semiconductor layer made of a compound semiconductor, an active layer on the N-type semiconductor layer, and a P-type semiconductor layer on the active layer. The LED is a kind of p-n junction diode and is a semiconductor device using electroluminescence, in which light is emitted when forward voltage is applied to the semiconductor device. The center wavelength of the light emitted from the LED is determined by bandgap energy (Eg) of a semiconductor used for the LED.

Temperature dependent electroluminescence (TDEL) method is most commonly used as a method for measuring internal quantum efficiency of the LED at a specific temperature (e.g., room temperature). In the method, it is assumed that the internal quantum efficiency ($\eta_{IQE}$) is 100% under a condition that the relative radiative efficiency ($\eta$) (i.e., $\eta=P/I$) defined as a ratio of the intensity (P) of light emitted from the LED to injection current (I) at an extremely low temperature (about 10K or less) is maximized, i.e., in the maximum injection current ($I_{max}$) having the maximum relative radiative efficiency ($\eta_{max}$) (i.e., $\eta_{max}=P_{max}/I_{max}$). The internal quantum efficiency ($\eta_{IQE}$) in predetermined injection current (I) at a specific temperature (e.g., room temperature) is obtained from a ratio of the relative radiative efficiency ($\eta=P/I$) under the same condition to the maximum relative radiative efficiency ($\eta_{max}=P_{max}/I_{max}$) at an extremely low temperature, i.e., $(P/I)/(P_{max}/I_{max})$. However, the case where it can be assumed that the internal quantum efficiency is 100% as the temperature becomes extremely lower is limited to the case where the maximum value of the relative radiative efficiency gradually increases to a specific maximum value as the temperature becomes lower. Also, it takes a very long time (about 5~6 hours) to change the temperature from an extremely low temperature to a room temperature, and a high-priced device for temperature tests is required. Since an extremely small portion of a wafer is to be cut and measured due to restriction of the size of a chamber in the device for temperature tests, the internal quantum efficiency of the entire wafer cannot be measured. The external quantum efficiency ($\eta_{EQE}$) defined as (number of photons coming out into free space per unit time)/(number of electrons injected in optical element) can be experimentally measured. The external quantum efficiency ($\eta_{EQE}$) is defined as a multiplication of internal quantum efficiency ($\eta_{IQE}$) and light extraction efficiency ($\eta_{extraction}$). Hence, if the internal quantum efficiency is to be measured, the internal quantum efficiency and the light extraction efficiency can be separately measured.

DISCLOSURE OF THE INVENTION

Technical Problem

The present invention provides a method and/or a device, which can measure internal quantum efficiency of a light emitting diode.

Technical Solution

Embodiments of the present invention provide methods for measuring efficiency of an optical element, the methods including: measuring an intensity P of light emitted from an optical element by applying an injection current I to the optical element; calculating a relative radiative efficiency $\eta$ from a ratio P/I of the intensity P of the emitted light to the injection current I; acquiring a maximum relative radiative efficiency and a maximum injection current corresponding to the maximum relative radiative efficiency; extracting a reference injection current $I_{ref}$ for minimizing an amount of change of a recombination coefficient in an active layer of the optical element with respect to a change of carrier concentration in the active layer of the optical element from data of injection currents equal to or less than the maximum injection current and data of relative radiative efficiencies equal to or less than the maximum relative radiative efficiency; calculating a reference internal quantum efficiency $\eta_{IQE,ref}$ of the optical element in the reference injection current; and calculating internal quantum efficiencies $\eta_{IQE}$ of the optical element in various injection currents from the reference internal quantum efficiency $\eta_{IQE,ref}$.

In some embodiments, the extracting of the reference injection current may include extracting the reference injection current $I_{ref}$ from a second parameter y at the point where the differentiation of b with respect to a first parameter x in curve $y=ax+bx^2$ of the second parameter y with respect to the first parameter x is minimized. The first parameter x may be $\sqrt{P/P_{normal}}$, and the second parameter y may be $I/I_{normal}$. Here, I is the injection current, $I_{normal}$ is a normal injection current equal to or less than the maximum injection current, P is the intensity of the emitted light, and $P_{normal}$ is a normal intensity of the emitted light in $I_{normal}$.

In other embodiments, the internal quantum efficiency $\eta_{IQE,ref}$ of the optical element in the reference injection current $I_{ref}$ may be expressed as $$\eta_{IQE,ref} = \frac{b_{ref}\left(\sqrt{P_{ref}/P_{normal}}\right)^2}{a_{ref}\sqrt{P_{ref}/P_{normal}} + b_{ref}\left(\sqrt{P_{ref}/P_{normal}}\right)^2}.$$

Here, $a_{ref}$ is the value of a in the reference injection current $I_{ref}$, $b_{ref}$ is the value of b in the reference injection current $I_{ref}$, and $P_{ref}$ is an intensity of the emitted light in the reference injection current $I_{ref}$.

In still other embodiments, the internal quantum efficiencies $\eta_{IQE}$ in the various injection currents I are expressed as $$\eta_{IQE} = \left(\frac{\eta}{\eta_{ref}}\right)\eta_{IQE,ref} = \left(\frac{P/I}{P_{ref}/I_{ref}}\right)\eta_{IQE,ref}.$$

Here, $\eta$ is a relative radiative efficiency calculated as P/I in the injection current I, and $\eta_{ref}$ is a relative radiative efficiency calculated as $P_{ref}/I_{ref}$ in the reference injection current $I_{ref}$.

In other embodiments of the present invention, devices for measuring efficiency of an optical element include: a light measurement unit configured to measure an intensity of light emitted from an optical element by applying an injection current to the optical element; and an operation unit configured to extract a reference injection current for minimizing the quadratic differential value of a curve of a second parameter y with respect to a first parameter x, calculate an internal quantum efficiency of the optical element in the reference injection current, and calculate internal quantum efficiencies of the optical element in various injection currents from the internal quantum efficiency of the optical element in the reference injection current, wherein the first parameter x is $\sqrt{P/P_{normal}}$, and the second parameter y is $I/I_{normal}$, wherein I is the injection current, $I_{normal}$ is a normal injection current equal to or less than the maximum injection current, P is the intensity of the emitted light, and $P_{normal}$ is a normal intensity of the emitted light in $I_{normal}$.

In some embodiments, the reference injection current $I_{ref}$ may be an injection current at the point where the differentiation of b with respect to the first parameter x in curve $y=ax+bx^2$ of the second parameter y with respect to the first parameter x is minimized.

In other embodiments, the internal quantum efficiency $\eta_{IQE,ref}$ of the optical element in the reference injection current $I_{ref}$ may be expressed as $$\eta_{IQE,ref} = \frac{b_{ref}\left(\sqrt{P_{ref}/P_{normal}}\right)^2}{a_{ref}\sqrt{P_{ref}/P_{normal}} + b_{ref}\left(\sqrt{P_{ref}/P_{normal}}\right)^2}.$$

Here, $a_{ref}$ is the value of a in the reference injection current $I_{ref}$, $b_{ref}$ is the value of b in the reference injection current $I_{ref}$, and $P_{ref}$ is an intensity of the emitted light in the reference injection current $I_{ref}$.

In still other embodiments, the internal quantum efficiencies $\eta_{IQE}$ in the various injection currents I are expressed as $$\eta_{IQE} = \left(\frac{\eta}{\eta_{ref}}\right)\eta_{IQE,ref} = \left(\frac{P/I}{P_{ref}/I_{ref}}\right)\eta_{IQE,ref}.$$

Here, $\eta$ is a relative radiative efficiency calculated as P/I in the injection current I, and $\eta_{ref}$ is a relative radiative efficiency calculated as $P_{ref}/I_{ref}$ in the reference injection current $I_{ref}$.

Advantageous Effects

By using the concept of the present invention, it is possible to non-destructively measure internal quantum efficiency within a short time (about 5 minutes) immediately after a light emitting diode is produced. Further, it is possible to separately measure internal quantum efficiency from external quantum efficiency in a chip or package state. Efficiencies of a light emitting diode are separately measured, so that it is possible to simply diagnose a cause such as where a defect occurs when the light emitting diode is produced.

MODE FOR CARRYING OUT THE INVENTION

Figure 1:
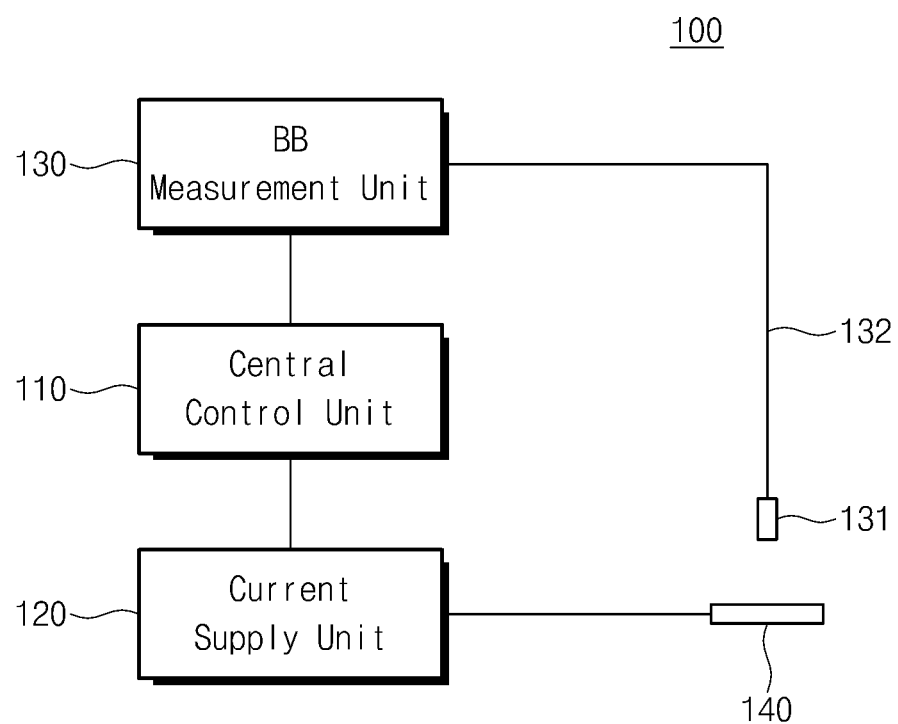
FIG. 1 is a view illustrating a device for measuring efficiency of an optical element according to an embodiment of the present invention.

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete and will fully convey the scope of the present invention to those skilled in the art. The reference numerals used in this description are not necessarily limited to the order presented.

Embodiments according to the technical scope of the present invention disclose a method for non-destructively measuring internal quantum efficiency of an optical element (e.g., a light emitting diode) at a normal or constant temperature. Carriers of the light emitting diode are excited by injection current and lose energy in the form of light emitted from the light emitting diode through recombination thereof.

FIG. 1 is a view illustrating a device 100 for measuring internal quantum efficiency of an optical element according to an embodiment of the present invention. Referring to FIG. 1, the device 100 includes a central control unit 110, a current supply unit 120 for applying injection current to an optical element 140, and a light measurement unit 130. The light measurement unit 130 may include an optical sensor 131 and an optical fiber 132. The optical element 140 may be a light emitting diode chip or a packaged light emitting diode.

The central control unit 110 controls the operation of the light measurement unit 130 and may calculate internal quantum efficiency of the optical element by collecting intensities of light emitted from the optical element 140 as the current supply unit 120 applies the injection current to the optical element. The central control unit 110 may include an operation unit 111 for calculating the internal quantum efficiency of the optical element. The light measurement unit 130 may communicate necessary data with the central control unit 110. The central control unit 110 may allow current having a desired intensity to be applied to the optical element 140 by transmitting a control signal to the current supply unit 120. The light measurement unit may detect light emitted from the optical element 140, generate a predetermined electrical signal corresponding to the intensity of the emitted light, and transmit the generated electrical signal to the central control unit 110.

Figure 2:
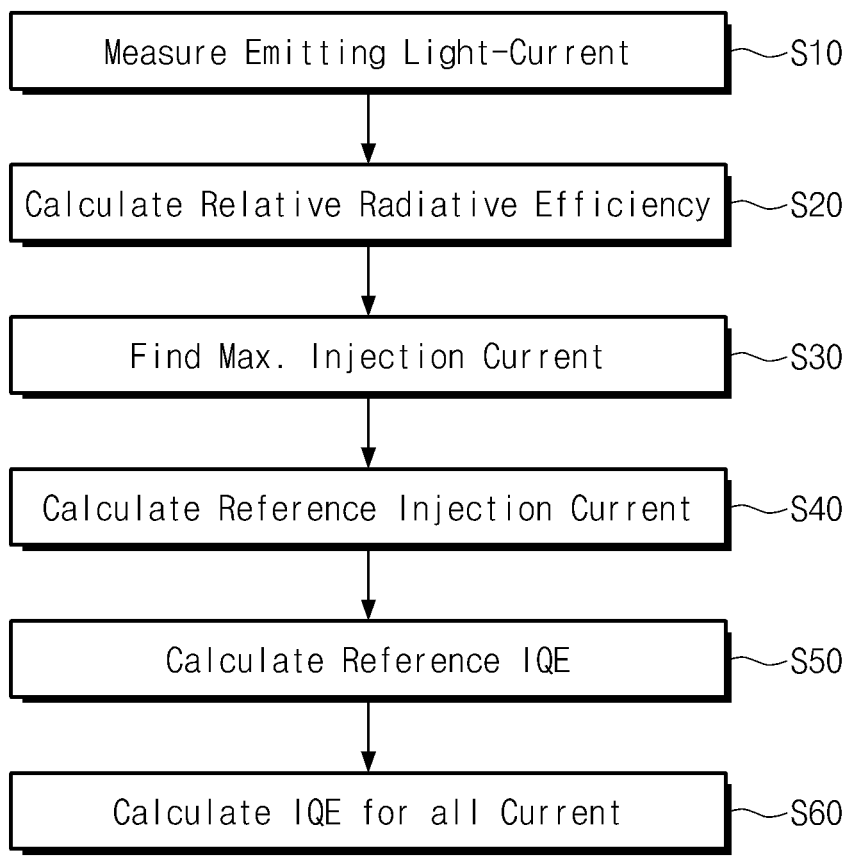
FIG. 2 is a flowchart in which internal quantum efficiency is evaluated according to an embodiment of the present invention.

FIG. 2 is a flowchart in which internal quantum efficiency is evaluated according to an embodiment of the present invention.

A method for calculating internal quantum efficiency of an optical element according to a change of the intensity of injection current in the operation unit of FIG. 1 will be described with reference to FIGS. 3 to 8.

Figure 3:
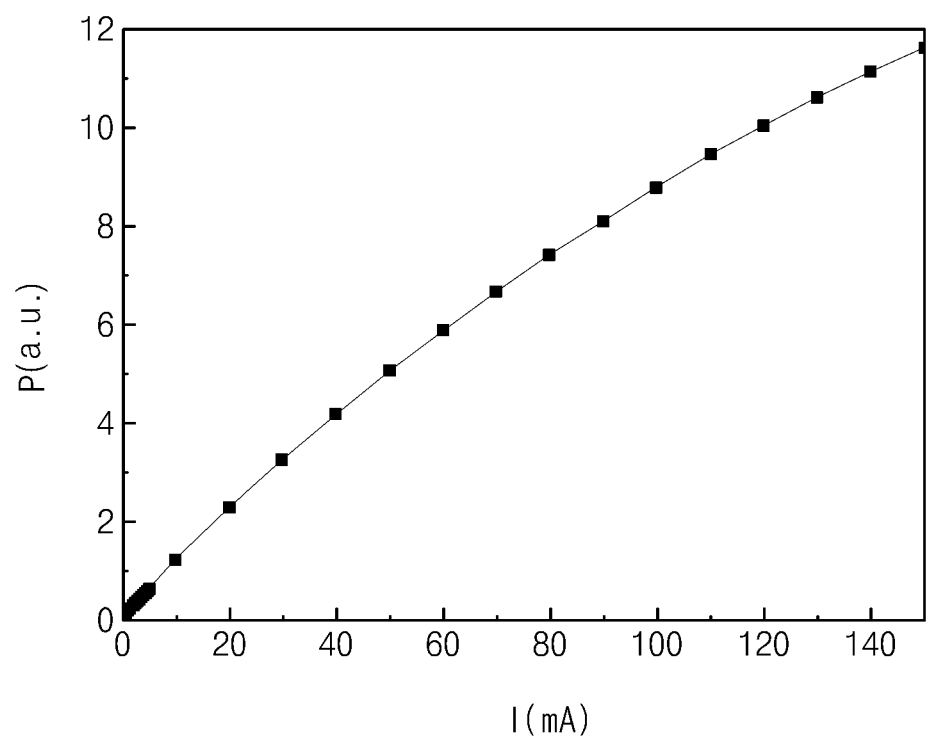
FIG. 3 is a graph showing intensities of light emitted from a light emitting diode, which are measured by applying injection currents to the light emitting diode.

Referring to FIGS. 2 and 3, the intensity P of light emitted from a light emitting diode may be measured by applying an injection current I to the light emitting diode (S10).

External quantum efficiency $\eta_{EQE}$ is frequently used as an index indicating the performance of the light emitting diode. The external quantum efficiency may be expressed as a multiplication of light extraction efficiency $\eta_{extraction}$, an injection efficiency $\eta_{injection}$, and a radiative efficiency $\eta_{radiative}$ as shown in the following Equation 1.

$$\eta_{EQE} = \eta_{extraction}\eta_{injection}\eta_{radiative} \qquad \text{Equation 1}$$

Here, the multiplication of the radiative efficiency $\eta_{radiative}$ and the injection efficiency $\eta_{injection}$ is defined as internal quantum efficiency $\eta_{IQE}$, and the radiative efficiency $\eta_{radiative}$ is generally expressed as a carrier rate equation as shown in Equation 2. Therefore, the external quantum efficiency $\eta_{EQE}$ may be expressed as a multiplication of the internal quantum efficiency $\eta_{IQE}$ and the light extraction efficiency $\eta_{extraction}$ as shown in Equation 2.

$$\eta_{EQE} = \eta_{extraction}\eta_{injection}\frac{B(N)N^2}{A(N)N + B(N)N^2} = \eta_{extraction}\eta_{IQE} \qquad \text{Equation 2}$$

Here, the external quantum efficiency $\eta_{EQE}$ may be defined by (the number of photons coming out into the free space per unit time)/(the number of electrons injected into the optical element per unit time), the internal quantum efficiency $\eta_{IQE}$ may be defined by (the number of photons generated in an active layer of the optical element per unit time)/(the number of electrons injected into the optical element per unit time), the injection efficiency $\eta_{injection}$ may be defined by (the number of electrons injected into the active layer of the optical element per unit time)/(the number of electrons injected into the optical element per unit time), the radiative efficiency $\eta_{radiative}$ may be defined by (the number of photons generated in the active layer of the optical element per unit time)/(the number of electrons injected in the active layer of the optical element per unit time), and the light extraction efficiency $\eta_{extraction}$ may be defined by (the number of photons coming out into the free space per unit time)/(the number of photons generated in the active layer of the optical element per unit time). In the carrier rate equation representing the radiative efficiency in Equation 2, A denotes a non-radiative recombination coefficient, B denotes a radiative recombination coefficient, and N denotes a carrier concentration of the active layer. A and B are expressed as a function of N. Hereinafter, the concept of relative radiative efficiency using an increase rate of the relative amount of light is used rather than the above-described external quantum efficiency based on the absolute amount of light.

Figure 4A:
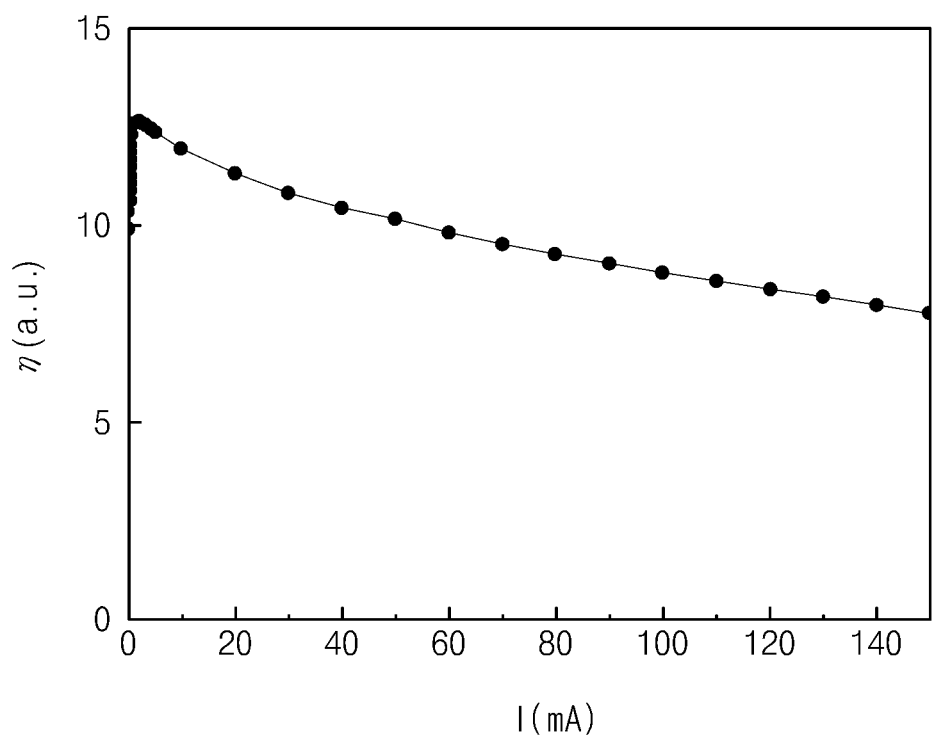
FIG. 4A is a graph showing relative radiative efficiencies ($\eta$) with respect to the injection currents obtained from FIG. 3.

Referring to FIGS. 2 and 4A, the relative radiative efficiency $\eta$ may be calculated by (intensity of light emitted)/(injection current), i.e., P/I (S20). A maximum relative radiative efficiency $\eta_{max}$ and a maximum injection current $I_{max}$ corresponding to the maximum relative radiative efficiency are acquired from FIG. 4B (S30).

Figure 4B:
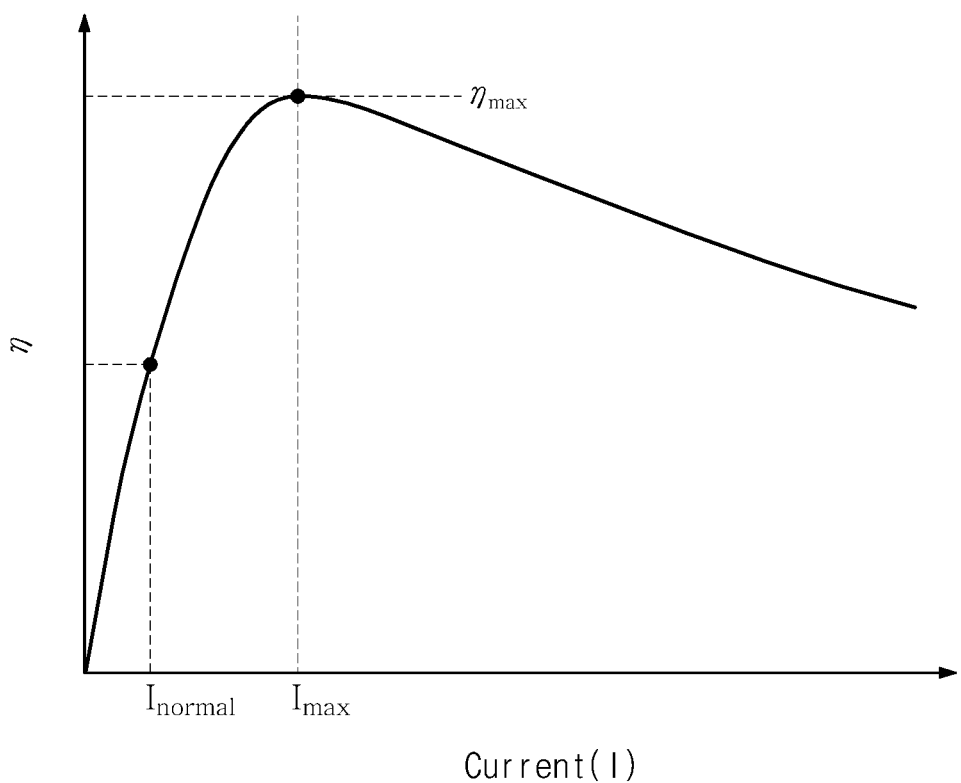
FIG. 4B is a conceptual view corresponding to FIG. 4A.
Figure 5:
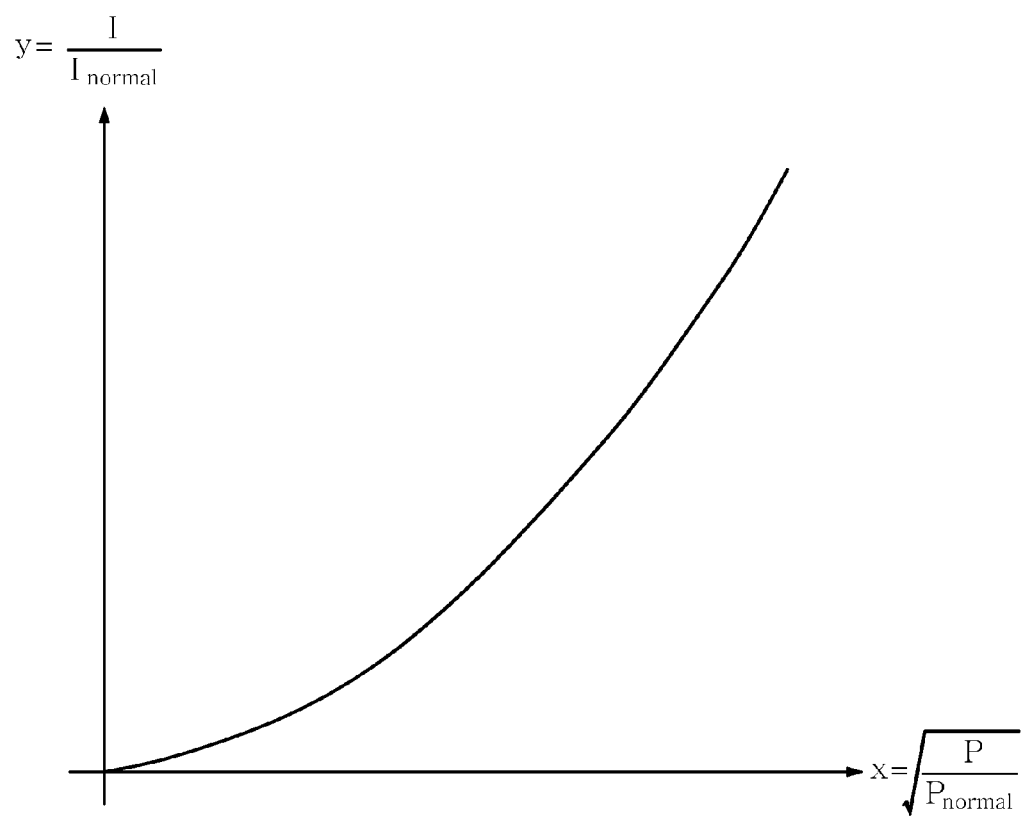
FIG. 5 is an x-y graph according to a model of the present invention.
Figure 6:
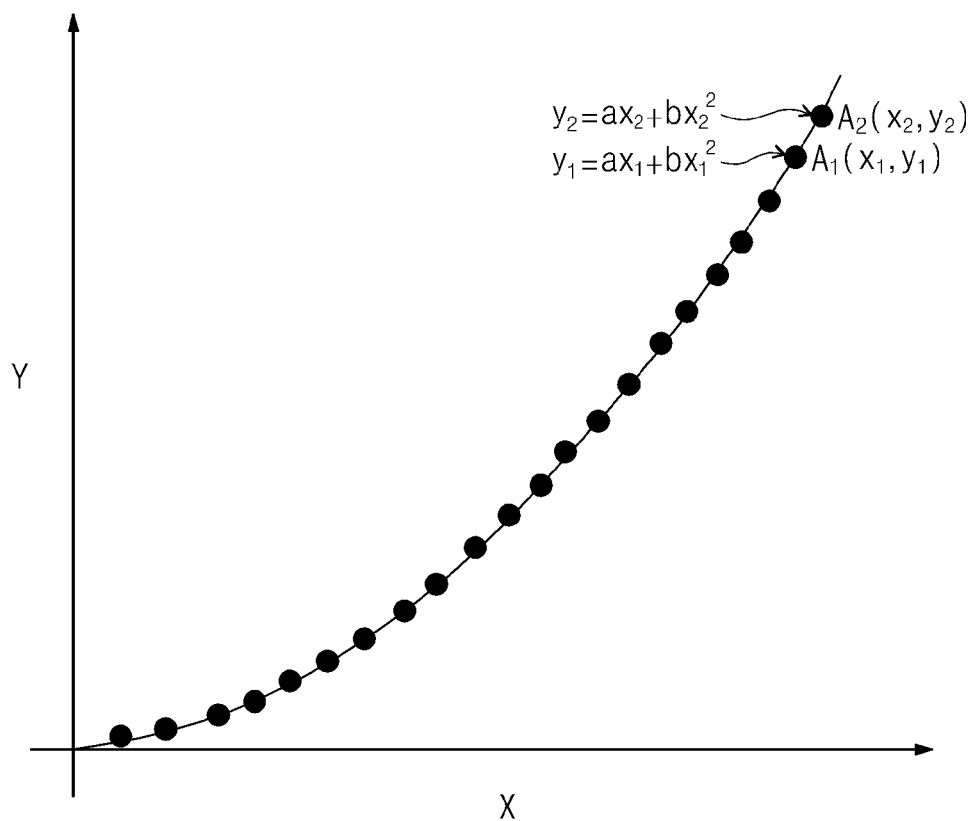
FIG. 6 illustrates two linear equations from data of two points A1 and A2 immediately adjacent to each other.

In FIG. 4B, in the region of injection currents equal to or less than the maximum relative radiative efficiency $\eta_{max}$, a change of the relative radiative efficiency is almost determined by a change of the radiative efficiency $\eta_{radiative}$. Since the light extraction efficiency $\eta_{extraction}$ is determined by the structure of the optical element, the light extraction efficiency may be regarded as a fixed constant which is not changed depending on an amount of injection current. When current starts flowing through the optical element, electrons injected from an electrode of the optical element first reach an active layer region having the lowest potential energy and are recombined. Hence, the injection efficiency becomes close to 100%. The following equations are considered at a section where the injection efficiency and the light extraction efficiency can be considered as constants because changes of the injection efficiency and the light extraction efficiency are sufficiently smaller than a change of the radiative efficiency as current is changed. In this instance, the considered injection current I is equal to or less than the maximum injection current $I_{max}$ corresponding to the maximum relative radiative efficiency $\eta_{max}$. That is, the range of data first considered in the present invention is a range of $0 < I < I_{max}$ (hereinafter, referred to as a consideration section).

When the process of radiative recombination is represented as the process of recombination of free carriers, the intensity P of the emitted light may be expressed as a multiplication of the radiative recombination coefficient B and the square of the carrier concentration N as shown in Equation 3.

$$P(N) = \eta_c(qV_a)B(N)N^2 \qquad \text{Equation 3}$$

Here, $V_a$ denotes a volume of the active layer of the light emitting diode, q denotes a charge amount of electrons, and $\eta_c$ denotes an optical coupling efficiency between a light emitting element and a light receiving element. Normal injection current $I_{normal}$ is an injection current which becomes a reference of normalization required in analyzing injection currents equal to or less than the maximum injection current $I_{max}$. The intensity P of the emitted light, which is measured in the normal injection current $I_{normal}$, is defined as a normal intensity $P_{normal}$ of the emitted light. The relative radiative efficiency in the normal injection current $I_{normal}$ is defined as a normal relative radiative efficiency $\eta_{normal}$ (i.e., $\eta_{normal} = P_{normal}/I_{normal}$). In the following embodiment, data were obtained using the maximum injection current $I_{max}$ corresponding to the maximum relative radiative efficiency $\eta_{max}$ as the normal injection current $I_{normal}$ (i.e., $I_{normal}=I_{max}$). The normal intensity $P_{normal}$ of the emitted light may be expressed as the following Equation 4.

$$P_{normal}=\eta_c(qV_a)B(N_{normal})N_{normal}^2 \qquad \text{Equation 4}$$

Here, $N_{normal}$ is a carrier concentration in the normal injection current $I_{normal}$. By dividing Equation 3 by Equation 4, the carrier concentration N may be expressed using only the intensity P of the emitted light and the radiative recombination coefficient B. This is expressed as the following Equation 5.

$$\frac{P(N)}{P(N_{normal})} = \frac{\eta_c(qV_a)B(N)N^2}{\eta_c(qV_a)B(N_{normal})N_{normal}^2} = \frac{B(N)N^2}{B(N_{normal})N_{normal}^2} \qquad \text{Equation 5}$$

$$N = N_{normal}\sqrt{\frac{P(N)}{P(N_{normal})}}\sqrt{\frac{B(N_{normal})}{B(N)}}$$

Meanwhile, from Equations 2 and 3, the injection current I may be expressed as the following Equation 6.

$$\eta_{injection}I=(qV_a)(A(N)N+B(N)N^2) \qquad \text{Equation 6}$$

The normal injection current $I_{normal}$ is expressed as the following Equation 7.

$$\eta_{injection}I_{normal}=(qV_a)(A(N_{normal})N_{normal}+B(N_{normal})N_{normal}^2) \qquad \text{Equation 7}$$

By dividing Equation 6 by Equation 7, the injection current I may be expressed as an equation of the radiative recombination coefficient B, the non-radiative recombination coefficient A, and the carrier concentration N. This is expressed as Equation 8.

$$\frac{I}{I_{normal}} = \frac{A(N)N + B(N)N^2}{A(N_{normal})N_{normal} + B(N_{normal})B_{normal}^2} \qquad \text{Equation 8}$$

If the carrier concentration N in Equation 5 is substituted in Equation 8, the injection current I is expressed as Equation 9.

$$\frac{I}{I_{normal}} = \frac{A(N)N_{normal}}{A(N_{normal})N_{normal} + B(N_{normal})N_{normal}^2}\sqrt{\frac{B(N_{normal})}{B(N)}}$$

$$\sqrt{\frac{P(N)}{P(N_{normal})}} + \frac{B(N)N_{normal}^2}{A(N_{normal})N_{normal} + B(N_{normal})N_{normal}^2}$$

$$\left(\sqrt{\frac{B(N_{normal})}{B(N)}}\sqrt{\frac{P(N)}{P(N_{normal})}}\right)^2 \qquad \text{Equation 9}$$

Equation 9 is simply expressed as Equation 10.

$$\frac{I}{I_{normal}} = a\sqrt{\frac{P(N)}{P(N_{normal})}} + b\left(\sqrt{\frac{P(N)}{P(N_{normal})}}\right)^2 \qquad \text{Equation 10}$$

wherein, $$a = \frac{A(N)N_{normal}}{A(N_{normal})N_{normal} + B(N_{normal})N_{normal}^2}\sqrt{\frac{B(N_{normal})}{B(N)}}$$

and $$b = \frac{B(N_{normal})N_{normal}^2}{A(N_{normal})N_{normal} + B(N_{normal})N_{normal}^2}.$$

Here, a is a function of the carrier concentration N, which is changed depending on A(N) and B(N), and b is a constant which is not changed depending on the carrier concentration N. In other words, the case where a mathematical model expressed as Equation 10 is applicable means that the coefficient of b should be a constant. In Equation 10, $I/I_{normal}$ and $\sqrt{P/P_{normal}}$ are values which can be measured at the outside. In this instance, P=P(N) and $P_{normal}=P(N_{normal})$. Thus, referring to FIG. 5, an x-y graph defined by $y=I/I_{normal}$ and $x=\sqrt{P/P_{normal}}$ can be obtained from the characteristic of the injection current of the light emitting diode–the intensity of the emitted light.

Figure 7:
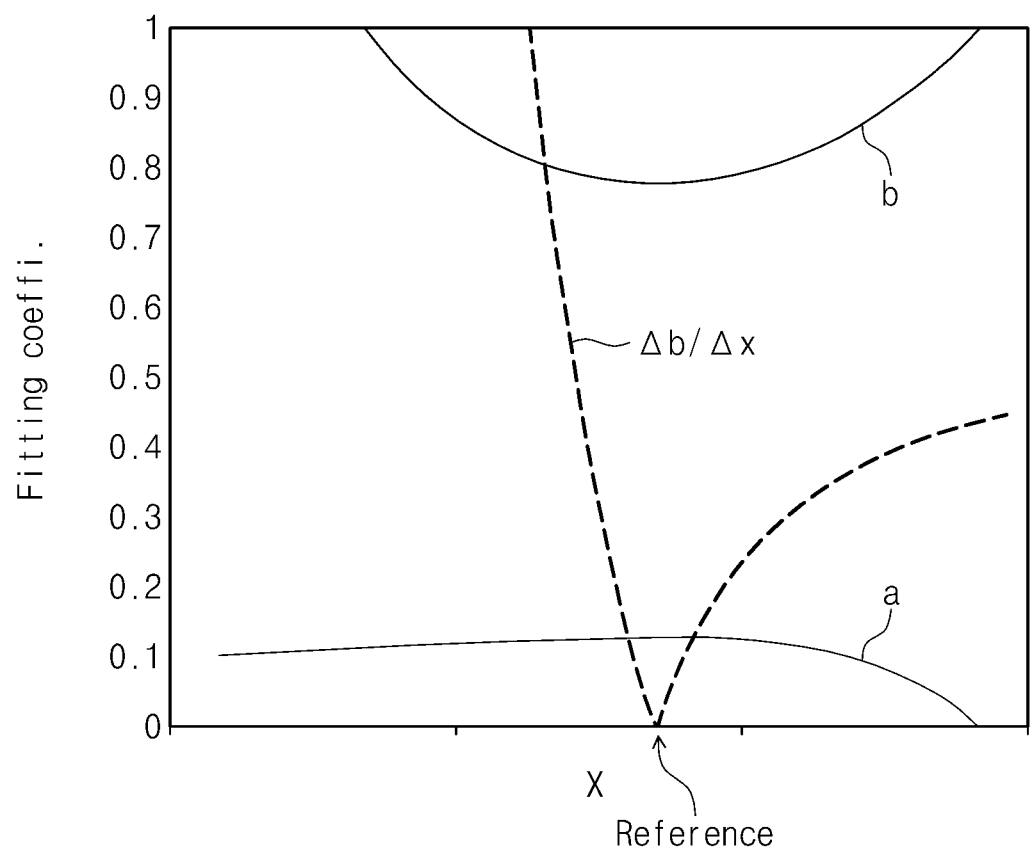
FIG. 7 illustrates results of a and b with respect to x and differentiation of the results.

The change ratio of a to b is very small as compared with that of x to y. Thus, referring to FIG. 6, two linear equations ($y_1=ax_1+bx_1^2$ and $y_2=ax_2+bx_2^2$) can be obtained from data (x1, y1, x2 and y2) of two points A1 and A2 immediately adjacent to each other. By solving the two linear equations, a and b at the section between the two points A1 and A2 can be obtained. Also, a and b may obtained at other points (i.e., the range of $0<I<I_{max}$). FIG. 7 illustrates results of a and b with respect to x in the consideration section.

Referring to FIG. 7, both of a and b are variables according to the carrier concentration N. From Equations 3 and 10 the x-axis is simply in proportion to the carrier concentration N. As described above, according to the model of the present invention, it is proper that a should be expressed as a function of the carrier concentration N, but b should be a constant which does not depend on the carrier concentration N. Here, it is assumed that the point at which the change ratio of h to the carrier concentration N is minimized (the point which can be expressed as a constant), i.e., the point at which the differentiation of h with respect to x is minimized (i.e., the point approaching zero) is a reference point. In other words, the quadratic differential value of a curve of a second parameter y with respect to a first parameter x is minimized. The model presented in Equation 2 can be most appropriate at the reference point. The injection current I at the reference point is defined as a reference injection current $I_{ref}$ (S40). Therefore, if a reference internal quantum efficiency $\eta_{IQE,ref}$ is calculated using the model presented in Equation 2, the reference internal quantum efficiency may be expressed as Equation 11 (S50).

$$\eta_{IQE,ref} = \frac{b_{ref}\left(\sqrt{P_{ref}/P_{normal}}\right)^2}{a_{ref}\sqrt{P_{ref}/P_{normal}} + b_{ref}\left(\sqrt{P_{ref}/P_{normal}}\right)^2} \qquad \text{Equation 11}$$

Here, $a_{ref}$, $b_{ref}$ and $P_{ref}$ are parameter a, parameter b, and intensity P of the emitted light in the reference current $I_{ref}$, respectively.

Internal quantum efficiencies $\eta_{IQE}$ in other various injection currents I may be obtained using the reference internal quantum efficiency $\eta_{IQE,ref}$. The characteristic of the entire measured injection current I-internal quantum efficiency $\eta_{IQE}$ may be obtained with reference to Equation 12 (S60).

$$\eta_{IQE} = \left(\frac{\eta}{\eta_{ref}}\right)\eta_{IQE,ref} \qquad \text{Equation 12}$$

Figure 8:
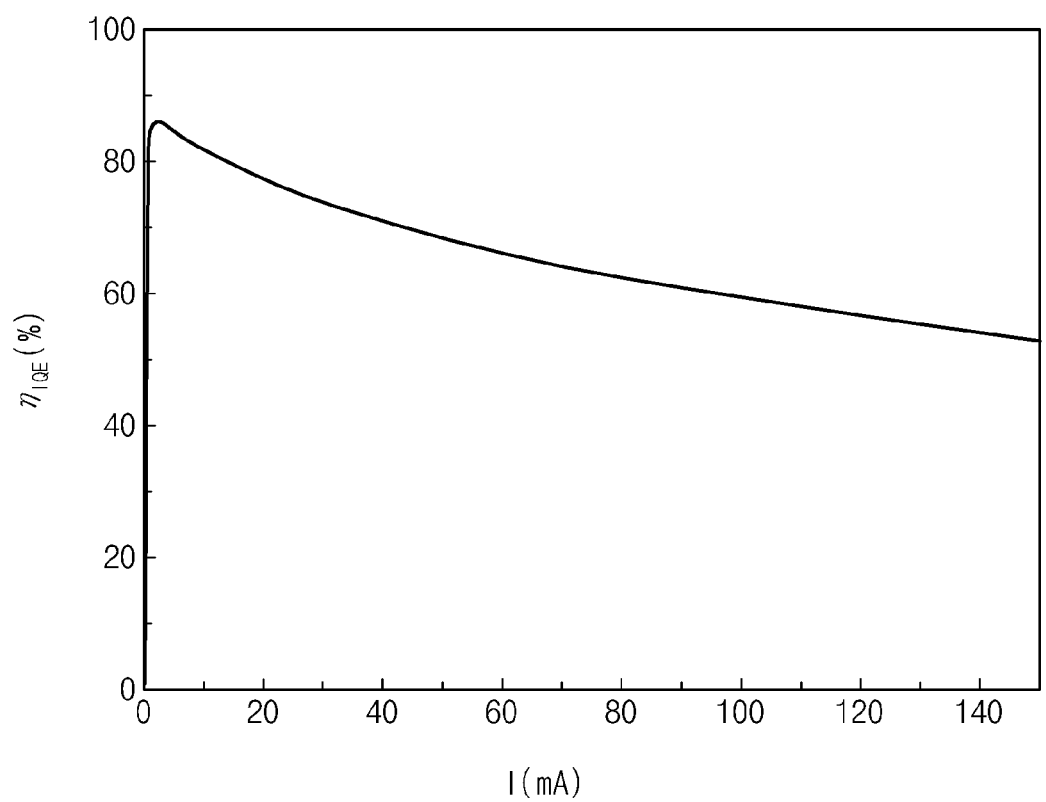
FIG. 8 is a graph of calculated injection currents-internal quantum efficiencies.

Here, $\eta$ and $\eta_{ref}$ are relative radiative efficiencies measured in the injection current I and the reference injection current $I_{ref}$, respectively. FIG. 8 is a graph of injection currents-internal quantum efficiencies, calculated by Equation 12. The graph is very similar to the actually measured graph of FIG. 2.

Figure 9:
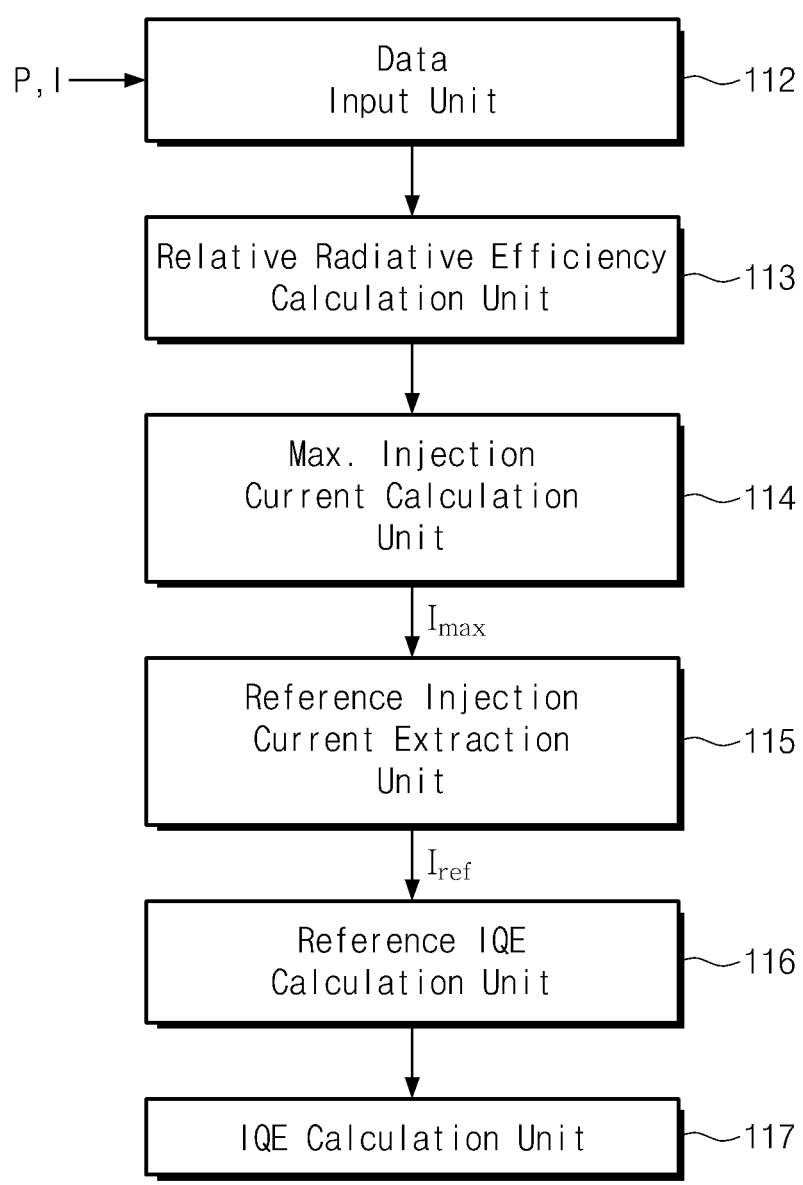
FIG. 9 is a view illustrating in detail an operation unit according to an embodiment of the present invention.

FIG. 9 is a view illustrating in detail an operation unit according to an embodiment of the present invention.

The calculation of efficiency of an optical element through the operation unit 111 constituting the central control unit of FIG. 1 will be described with reference to FIG. 9. The operation unit 111 according to the embodiment of the present invention may perform the above-described steps of FIG. 2. The operation unit 111 may include a data input unit 112, an external quantum efficiency calculation unit 113, a maximum injection current calculation unit 114, a reference injection current extraction unit 115, a reference internal quantum efficiency calculation unit 116, and an internal quantum efficiency calculation unit 117.

The data input unit 112 collects intensities P of light emitted from the optical element, which are output from the light measurement unit 130. The relative radiative efficiency calculation unit 113, as shown in S20, calculates a relative radiative efficiency from a ratio P/I of the intensity P of the emitted light to the injection current I. The maximum injection current calculation unit 114, as shown in S30, acquires the maximum relative radiative efficiency and the maximum injection current $I_{max}$ corresponding thereto from data of relative radiative efficiencies in the relative radiative efficiency calculation unit 113. The reference injection current extraction unit 115, as shown in S40, extracts a reference injection current $I_{ref}$. The reference internal quantum efficiency calculation unit 116, as shown in S50, calculates an internal quantum efficiency $\eta_{IQE,ref}$ of the optical element in the intensity of the reference injection current. The internal quantum efficiency calculation unit 117, as shown in S60, calculates internal quantum efficiencies $\eta_{IQE}$ in various injection currents.

Figure 10:
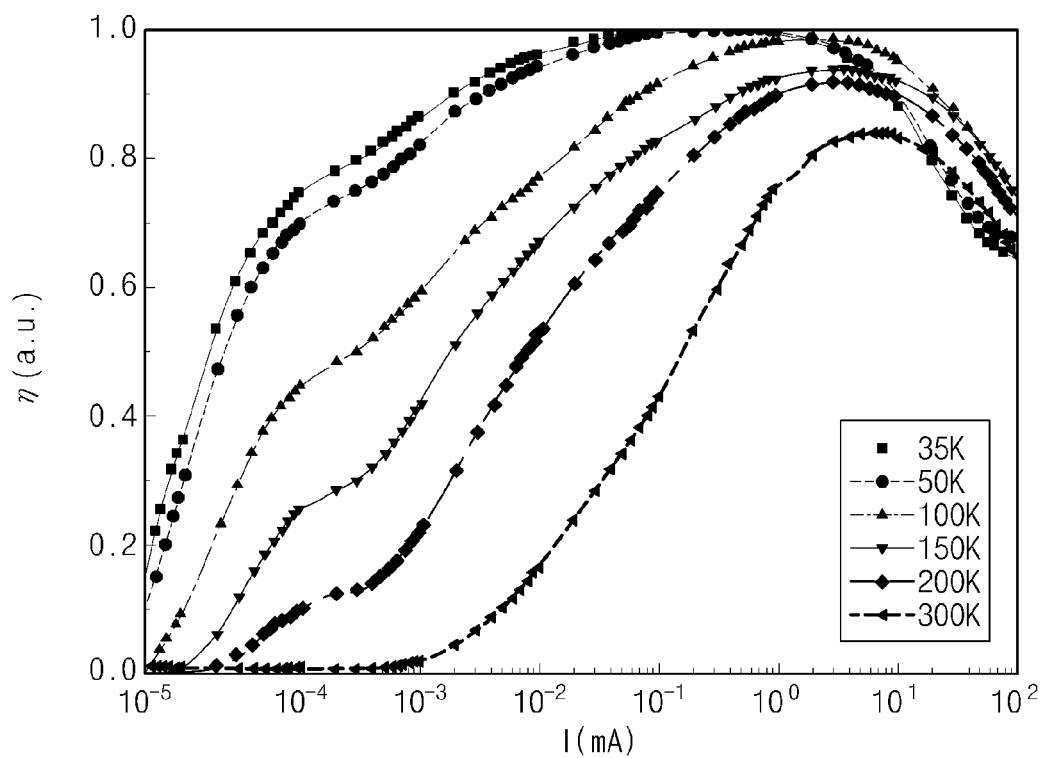
FIG. 10 illustrates ratios of the maximum relative radiative efficiency near the absolute temperature to relative radiative efficiencies at a plurality of temperatures.

FIG. 10 illustrates ratios of the maximum relative radiative efficiency near the absolute temperature to relative radiative efficiencies at a plurality of temperatures. The relative radiative efficiency near the absolute temperature is saturated regardless of temperature. Accordingly, the energy loss caused by the non-radiative recombination (A) is very small as compared with the radiative recombination of carriers near the absolute temperature, and thus it can be assumed that the internal quantum efficiency is 100%. FIG. 10 illustrates results obtained by measuring internal quantum efficiencies at a plurality of temperatures through the temperature dependent electroluminescence (TDEL) method based on the above-described view point.

Figure 11:
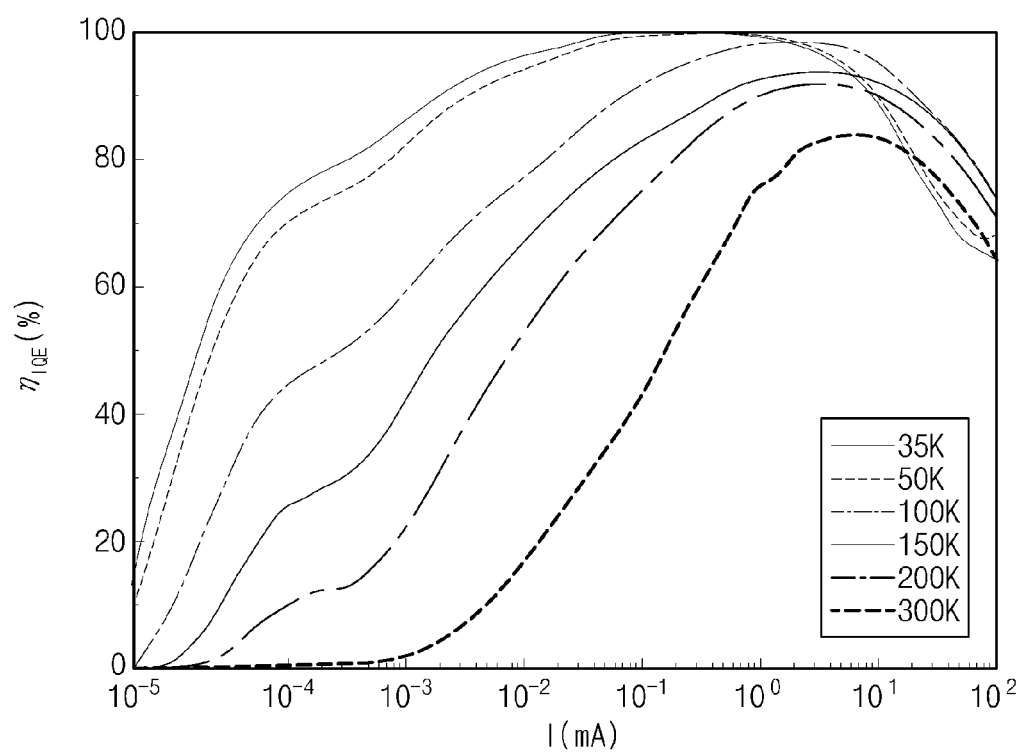
FIG. 11 illustrates internal quantum efficiencies at a plurality of temperatures, which is obtained according to the model of the present invention.

FIG. 11 illustrates internal quantum efficiencies at a plurality of temperatures, obtained according to the model of the present invention. The result obtained in FIG. 8 is very similar to actually measured data of FIG. 10.

By using the concept of the present invention, it is possible to non-destructively measure internal quantum efficiency within a short time (about 5 minutes) immediately after a light emitting diode is produced. Further, it is possible to separately measure internal quantum efficiency $\eta_{IQE,ref}$ from relative radiative efficiency $\eta$ in a chip or package state.

INDUSTRIAL APPLICABILITY

Efficiencies of a light emitting diode are separately measured, so that it is possible to simply diagnose a cause such as where a defect occurs when the light emitting diode is produced.

The invention claimed is:

1. A method for measuring efficiency of physical optical element having an active semiconductor layer for use with an electronic device having a central control unit, a current supply unit to apply injection current to the optical element, and a light measurement unit, the method comprising:
    measuring, via the light measurement unit, an intensity P of light emitted from the physical optical element by applying an injection current I from the current supply unit to the physical optical element;
    calculating, via the central control unit, a relative radiative efficiency $\eta$ from a ratio P/I of the intensity P of the emitted light to the injection current I;
    acquiring, via the central control unit, a maximum relative radiative efficiency and a maximum injection current corresponding to the maximum relative radiative efficiency;
    extracting, via the central control unit, a reference injection current $I_{ref}$ for minimizing an amount of change of a recombination coefficient in the active semiconductor layer of the physical optical element with respect to a change of carrier concentration in the active semiconductor layer of the physical optical element from data of injection currents equal to or less than the maximum injection current and data of relative radiative efficiencies equal to or less than the maximum relative radiative efficiency;
    calculating, via the central control unit, a reference internal quantum efficiency $\eta_{IQE,ref}$ of the physical optical element in the reference injection current; and
    calculating, via the central control unit, internal quantum efficiencies $\eta_{IQE}$ of the physical optical element in various injection currents from the reference internal quantum efficiency $\eta_{IQE,ref}$.

2. The method of claim 1, wherein the extracting of the reference injection current includes extracting the reference injection current $I_{ref}$ from a second parameter y at the point where the differentiation of b with respect to a first parameter x in curve y=ax+bx² of the second parameter y with respect to the first parameter x is minimized,
    wherein the first parameter x is $\sqrt{P/P_{normal}}$, and the second parameter y is $I/I_{normal}$,
    wherein I is the injection current, $I_{normal}$ is a normal injection current equal to or less than the maximum injection current, P is the intensity of the emitted light, and $P_{normal}$ is a normal intensity of the emitted light in $I_{normal}$.

3. The method of claim 2, wherein the internal quantum efficiency $\eta_{IQE,ref}$ of the optical element in the reference injection current $I_{ref}$ is expressed as $$\eta_{IQE,ref} = \frac{b_{ref}\left(\sqrt{P_{ref}/P_{normal}}\right)^2}{a_{ref}\sqrt{P_{ref}/P_{normal}} + b_{ref}\left(\sqrt{P_{ref}/P_{normal}}\right)^2},$$

wherein $a_{ref}$ is the value of a in the reference injection current $I_{ref}$, $b_{ref}$ is the value of b in the reference injection current $I_{ref}$, and $P_{ref}$ is an intensity of the emitted light in the reference injection current $I_{ref}$.

4. The method of claim 2, wherein the internal quantum efficiencies $\eta_{IQE}$ of the optical element in the various injection currents I are expressed s $$\eta_{IQE} = \left(\frac{\eta}{\eta_{ref}}\right)\eta_{IQE,ref} = \left(\frac{P/I}{P_{ref}/I_{ref}}\right)\eta_{IQE,ref},$$

wherein η is a relative radiative efficiency calculated as P/I in the injection current I, and $\eta_{ref}$ is a relative radiative efficiency calculated as $P_{ref}/I_{ref}$ in the reference injection current $I_{ref}$.

5. An electronic device for measuring efficiency of an optical element having an active semiconductor layer, the electronic device comprising:
   a current supply unit configured to apply an injection current;
   a light measurement unit configured to measure an intensity of light emitted from an optical element by applying the injection current from the current supply unit to the optical element; and
   an operation unit configured to extract a reference injection current for minimizing the quadratic differential value of a curve of a second parameter y with respect to a first parameter x, calculate an internal quantum efficiency of the optical element in the reference injection current, and calculate internal quantum efficiencies of the optical element in various injection currents from the internal quantum efficiency of the optical element in the reference injection current, wherein the first parameter x is $\sqrt{P/P_{normal}}$, and the second parameter y is $I/I_{normal}$,
   wherein I is the injection current, $I_{normal}$ is a normal injection current equal to or less than the maximum injection current, P is the intensity of the emitted light, and $P_{normal}$ is a normal intensity of the emitted light in $I_{normal}$.

6. The device of claim 5, wherein the reference injection current $I_{ref}$ is an injection current at the point where the differentiation of b with respect to the first parameter x in curve $y=ax+bx^2$ of the second parameter y with respect to the first parameter x is minimized.

7. The device of claim 6, wherein the internal quantum efficiency $\eta_{IQE,ref}$ of the optical element in the reference injection current $I_{ref}$ is expressed as $$\eta_{IQE,ref} = \frac{b_{ref}\left(\sqrt{P_{ref}/P_{normal}}\right)^2}{a_{ref}\sqrt{P_{ref}/P_{normal}} + b_{ref}\left(\sqrt{P_{ref}/P_{normal}}\right)^2},$$

wherein $a_{ref}$ is the value of a in the reference injection current $I_{ref}$, $b_{ref}$ is the value of b in the reference injection current $I_{ref}$, and $P_{ref}$ is an intensity of the emitted light in the reference injection current $I_{ref}$.

8. The device of claim 7, wherein the internal quantum efficiencies $\eta_{IQE}$ of the optical element in the various injection currents I are expressed as $$\eta_{IQE} = \left(\frac{\eta}{\eta_{ref}}\right)\eta_{IQE,ref} = \left(\frac{P/I}{P_{ref}/I_{ref}}\right)\eta_{IQE,ref},$$

wherein η is a relative radiative efficiency calculated as P/I in the injection current I, and $\eta_{ref}$ is a relative radiative efficiency calculated as $P_{ref}/I_{ref}$ in the reference injection current $I_{ref}$.

* * * * *